United States Patent
Martinez-Arocho et al.

(10) Patent No.: US 11,133,107 B2
(45) Date of Patent: *Sep. 28, 2021

(54) MACHINE LEARNING ALLERGY RISK DIAGNOSIS DETERMINATION

(71) Applicant: INTERNATIONAL BUSINESS MACHINES CORPORATION, Armonk, NY (US)

(72) Inventors: Allison G. Martinez-Arocho, Raleigh, NC (US); Randy A. Rendahl, Raleigh, NC (US); Jocelyn Sese, Wake, NC (US); Ashley K. Silva, Durham, NC (US)

(73) Assignee: International Business Machines Corporation, Armonk, NY (US)

( * ) Notice: Subject to any disclaimer, the term of this patent is extended or adjusted under 35 U.S.C. 154(b) by 456 days.

This patent is subject to a terminal disclaimer.

(21) Appl. No.: 15/817,485

(22) Filed: Nov. 20, 2017

(65) Prior Publication Data

US 2019/0155992 A1 May 23, 2019

(51) Int. Cl.
*G16H 20/60* (2018.01)
*G16H 50/20* (2018.01)
*G16H 50/30* (2018.01)
*G16H 40/60* (2018.01)
*G16H 10/60* (2018.01)
(Continued)

(52) U.S. Cl.
CPC ............ *G16H 50/20* (2018.01); *G16H 10/60* (2018.01); *G16H 15/00* (2018.01); *G16H 40/60* (2018.01);
(Continued)

(58) Field of Classification Search
CPC ........ G16H 50/20; G16H 10/60; G16H 50/30; G16H 20/00; G06Q 30/0627; G06Q 50/12; G06Q 50/22–24; A61B 5/411
See application file for complete search history.

(56) References Cited

U.S. PATENT DOCUMENTS 6,865,261 B1 3/2005 Rao et al.
7,953,873 B1 * 5/2011 Madurzak ............ G06Q 30/02
709/229

(Continued)

OTHER PUBLICATIONS

Bradley, Jeanette; Food Allergy Apps to Help Keep You Safe; URL: https://www.verywell.com/food-allergy-apps-to-help-keep-you-safe-1324320; Oct. 22, 2017; 19 pages.
(Continued)

*Primary Examiner* — Robert W Morgan
*Assistant Examiner* — Emily Huynh
(74) *Attorney, Agent, or Firm* — Schmeiser, Olsen & Watts; Nicholas L. Cadmus

(57) ABSTRACT

A system for improving a machine learning allergy diagnosis process is provided. The system implements a method that includes identifying databases comprising data identifying menu items served by food establishments. Allergy data defining a food products associated with potential allergens is analyzed in real time and in response, baseline allergen indication software code for defining an allergen baseline indicator is generated. Ingredients of the menu items are analyzed with respect to the allergy data and allergen baseline levels for the ingredients determined. An allergen baseline level for each menu item is determined and an allergen alert software application for alerting a user with respect to each overall allergen assessment is generated.

8 Claims, 6 Drawing Sheets

(51) Int. Cl.
*G16H 15/00* (2018.01)
*G06Q 50/12* (2012.01)
*G06Q 30/06* (2012.01)
*G06N 20/00* (2019.01)

(52) U.S. Cl.
CPC .............. *G16H 50/30* (2018.01); *G06N 20/00* (2019.01); *G06Q 30/0627* (2013.01); *G06Q 50/12* (2013.01)

(56) References Cited

U.S. PATENT DOCUMENTS

| | | | |
|---|---|---|---|
| 9,449,336 B2 | 9/2016 | Wilson et al. | |
| 2010/0161432 A1 | 6/2010 | Kumanov et al. | |
| 2011/0318717 A1 | 12/2011 | Adamowicz | |
| 2012/0094258 A1* | 4/2012 | Langheier | G16H 40/63 434/127 |
| 2015/0248651 A1* | 9/2015 | Akutagawa | G06Q 50/01 705/7.19 |
| 2016/0091419 A1 | 3/2016 | Watson et al. | |
| 2016/0171514 A1* | 6/2016 | Frank | G06Q 30/02 705/7.29 |
| 2017/0215016 A1* | 7/2017 | Dohmen | A61B 5/6817 |
| 2017/0239418 A1* | 8/2017 | Levine | A61K 31/137 |
| 2018/0070873 A1* | 3/2018 | Cronin | G16H 50/30 |
| 2018/0165588 A1* | 6/2018 | Saxena | G06F 19/324 |
| 2020/0051697 A1* | 2/2020 | Krishnamurti | G16H 10/20 |

OTHER PUBLICATIONS

Asthma & Allergy Center; Legal Information; URL: https://www.asthmaandallergycenter.net/legal; Retrieved from the Internet Feb. 25, 2017; 2 pages.

Webicin; Allergy and Social Media; URL: https://www.webicina.com/allergy; retrieved from the Internet Feb. 25, 2017; 3 pages.

FARE; Food Allergy Research & Education; URL: https://www.foodallergy.org/, retrieved from the Internet Feb. 25, 2017; 5 pages.

Best Allergy Sites; New Food Allergy App: Content Checked; URL: http://www.bestallergysites.com/food-allergy-app-content-checked/; retrieved from the Internet Feb. 25, 2017; 6 pages.

Allergy Eats; Out Story; URL: https://www.allergyeats.com/about-us/mission-statement/, retrieved from the Internet Feb. 25, 2017; 2 pages.

Pistiner, Michael, MD, MMSc; Superman, Food, Allergy and Social Media; Blog@AllergyHome.org; URL: https://www.allergyhome.org/blogger/superman-food-allergy-and-social-media/; Nov. 9, 2013; 6 pages.

Fleming, Anthony; Top Resaurant Apps for Dairy-Free, Vegan, and Food Allergies; GoDairyFree.com; Aug. 4, 2014; 13 pages.

Marshall, Donna et al.; What's Your Strategy for Supply Chain Disclosure; MIT Sloan Management Review Winter 2016; Dec. 14, 2015; 4 pages.

Califf, Robert M., MD; Report to Congress on Enhancing Tracking and Tracing of Food and Recordkeeping; Nov. 16, 2016; 28 pages.

Tanno, L. K. et al.; Constructing a classification of hypersensitivity/allergic diseases for ICD-11 by crowdsourcing the allergist community; Allergy, European Journal of Allergy and Clinical Immunology; vol. 70; Mar. 1, 2015; 7 pages.

Dimov, Ves et al.; Utilizing social networks, blogging and YouTube in allergy and immunology practices; Expert Review of Clinical Immunology, 11:10; Jul. 10, 2015; pp. 1065-1068.

\* cited by examiner

MACHINE LEARNING ALLERGY RISK DIAGNOSIS DETERMINATION

FIELD

The present invention relates generally to a method for monitoring allergy based conditions with respect to a user and in particular to a method and associated system for improving allergen alert software technology associated with enabling sensors for detecting biometric levels of a user and executing associated actions for automatically generating software code instructions.

BACKGROUND

Accurately determining user issues typically includes an inaccurate process with little flexibility. Controlling devices associated with preventing the user issues may include a complicated process that may be time consuming and require a large amount of resources. Accordingly, there exists a need in the art to overcome at least some of the deficiencies and limitations described herein above.

SUMMARY

A first aspect of the invention provides a machine learning allergy risk diagnosis improvement method comprising: identifying, by a processor of a server hardware device, a plurality of databases comprising data identifying menu items served by a plurality of food establishments; first analyzing in real time, by the processor executing natural language software code, allergy data defining a plurality of food products associated with a plurality of potential allergens; generating, by the processor based on results of the analyzing, baseline allergen indication software code for defining an allergen baseline indicator; second analyzing in real time, by the processor executing the natural language software code and the baseline allergen indication software code, ingredients of the menu items with respect to the allergy data; determining, by the processor based on results of the second analyzing in real time, allergen baseline levels for the ingredients of the menu items; determining, by the processor, an overall allergen assessment for each menu item of the menu items; and generating, by the processor, an allergen alert software application for alerting users with respect to each the overall allergen assessment.

A second aspect of the invention provides computer program product, comprising a computer readable hardware storage device storing a computer readable program code, the computer readable program code comprising an algorithm that when executed by a processor of a server hardware device implements a machine learning allergy risk diagnosis improvement method, the method comprising: identifying, by the processor, a plurality of databases comprising data identifying menu items served by a plurality of food establishments; first analyzing in real time, by the processor executing natural language software code, allergy data defining a plurality of food products associated with a plurality of potential allergens; generating, by the processor based on results of the analyzing, baseline allergen indication software code for defining an allergen baseline indicator; second analyzing in real time, by the processor executing the natural language software code and the baseline allergen indication software code, ingredients of the menu items with respect to the allergy data; determining, by the processor based on results of the second analyzing in real time, allergen baseline levels for the ingredients of the menu items; determining, by the processor, an allergen baseline levels for each menu item of the menu items; and generating, by the processor, an allergen alert software application for alerting users with respect to each the overall allergen assessment.

A third aspect of the invention provides server hardware device comprising a processor coupled to a computer-readable memory unit, the memory unit comprising instructions that when executed by the computer processor implements a machine learning allergy risk diagnosis improvement method comprising: identifying, by the processor, a plurality of databases comprising data identifying menu items served by a plurality of food establishments; first analyzing in real time, by the processor executing natural language software code, allergy data defining a plurality of food products associated with a plurality of potential allergens; generating, by the processor based on results of the analyzing, baseline allergen indication software code for defining an allergen baseline indicator; second analyzing in real time, by the processor executing the natural language software code and the baseline allergen indication software code, ingredients of the menu items with respect to the allergy data; determining, by the processor based on results of the second analyzing in real time, allergen baseline levels for the ingredients of the menu items; determining, by the processor, an allergen baseline levels for each menu item of the menu items; and generating, by the processor, an allergen alert software application for alerting users with respect to each the overall allergen assessment.

The present invention advantageously provides a simple method and associated system capable of accurately determining user issues.

DETAILED DESCRIPTION

Figure 1:
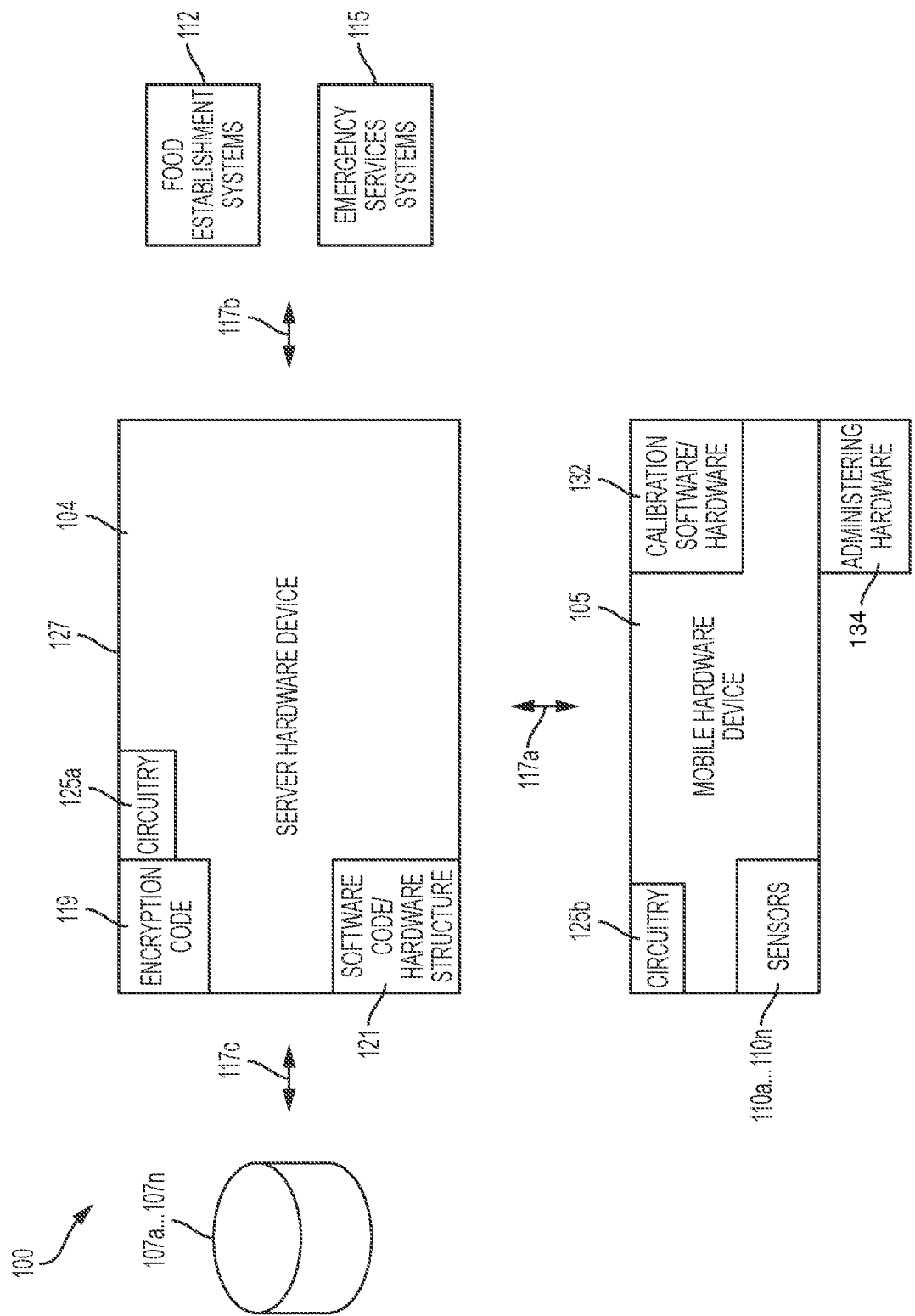
FIG. 1 illustrates a system for improving machine learning allergy risk diagnosis technology associated with enabling sensors for monitoring user conditions and executing associated actions for automatically updating software and notifying authorized personnel, in accordance with embodiments of the present invention.

FIG. 1 illustrates a system 100 for improving machine learning allergy risk diagnosis technology associated with enabling sensors for monitoring user conditions and executing associated actions for automatically updating software and notifying authorized personnel, in accordance with embodiments of the present invention. System 100 enables a process for automatically generating software for providing rankings for restaurants based on a user's food allergy information (i.e., comprising a potential for causing an allergic reaction). The generated software executes a process for receiving database retrieved supply chain data and applying natural language processing code to the supply chain data to identify user allergens and associated solution actions.

System 100 enables a process for automatically processing data (via execution of machine learning code) simultaneously retrieved (in real time) from multiple Web-scraped (i.e., an automated process implemented using a bot or web crawler.) sources and combined with known user information to provide personalized restaurant and menu recommendations. Results of the processed data are presented (via a graphical user interface (GUI)) in the form of a grading/rating system for effectively communicating the convenience and safety of any given restaurant according to an individual's dietary needs. Additionally, a personalized safety rating is automatically generated based on a comprehensive allergen analysis of a restaurant and a sensitivity profile of the diner(s).

System 100 of FIG. 1 includes a server hardware device 104 (i.e., specialized hardware device), a mobile hardware device 105 (i.e., specialized hardware device), food establishment systems 112, emergency services systems 115, and a database system 107a . . . 107n interconnected through a network 117a, 117b, and 117c. Server hardware device 104 includes specialized circuitry 125a (that may include specialized software), encryption code 119 (for encrypting any output) and software code 121. Mobile hardware device 105 may include a personal food restriction device provided and registered to all users with food restrictions. Mobile hardware device 105 may be Bluetooth (or near field communication, etc.) enabled to provide connectivity to a food establishment systems 112. Mobile hardware device 105 provides a registered ID linking to a central profile storing a user's defined food restrictions. Mobile hardware device 105 includes specialized circuitry 125b (that may include specialized software), calibration software/hardware, sensors 110a . . . 110n, and administering hardware 134. Sensors 110a . . . 110n may include any type of internal or external biomedical sensors including, inter alia, a heart rate monitor, a blood pressure monitor, a temperature sensor, a pulse rate monitor, an ultrasonic sensor, an optical sensor, a video retrieval device, humidity sensors, etc. Administering hardware 134 may comprise devices for automatically administering an allergic reaction substance to a user in response to a detected allergy issue. For example, administering hardware 134 may include a controller for activating a solenoid for initializing an epinephrine administering device for administering epinephrine to a user experiencing an allergic reaction. Additionally, administering hardware 134 may comprise automated medical devices and associated automated controllers for automatically modifying biomedical attributes of the user. Calibration software/hardware 132 may include specialized testing circuitry/logic. Server hardware device 104, mobile hardware device 105, and database system 107a . . . 107n may each comprise an embedded device. An embedded device is defined herein as a dedicated device or computer comprising a combination of computer hardware and software (fixed in capability or programmable) specifically designed for executing a specialized function. Programmable embedded computers or devices may comprise specialized programming interfaces. In one embodiment, server hardware device 104, mobile hardware device 105, and database system 107a . . . 107n may each comprise a specialized hardware device comprising specialized (non-generic) hardware and circuitry (i.e., specialized discrete non- generic analog, digital, and logic based circuitry) for (independently or in combination) executing a process described with respect to FIGS. 1-5. The specialized discrete non-generic analog, digital, and logic based circuitry may include proprietary specially designed components (e.g., a specialized integrated circuit, such as for example an Application Specific Integrated Circuit (ASIC) designed for only implementing an automated process for improving machine learning medical issue determination technology. Network 117a, 117b, and 117c may include any type of network including, inter alia, a local area network, (LAN), a wide area network (WAN), the Internet, a wireless network, etc. Alternatively, network 117a, 117b, and 117c may include application programming interfaces (API). Food establishment systems 112 may include a provider presence device for communicating (via Bluetooth) with mobile hardware device 105 to identify profiles determining food restrictions for a group of users. The provider presence device continuously retrieves notifications of restrictions and provides a self-service hardware/software interface for the group to evaluate a food establishment's compatibility with the group's restrictions. A membership to a group may be implemented based on a set proximity threshold and augmented by providing a list of discovered devices of the group. Additionally, the provider presence device requires access to the Internet for connectivity with server hardware device 104.

The following implementation example (executed by system 100) describes a process for improving machine learning medical issue determination technology with respect to executing continuously running software code (in real time) for gathering and profiling restaurants and associated menu content:

Potential database sources are identified for each restaurant in the database. Data sources may include, inter alia, Web content supplied by a participating restaurant, supplier data associated with a restaurant, etc. Supply chain content (for each allergen source) is run (in real time) through a natural language processor to locate products matching a populated vocabulary of allergens. A resulting output is enabled to provide a baseline allergen indication such as no allergen or allergen. Additionally, restaurant recipes are run through the natural language processor to locate items that have been identified as allergen-containing in the supply chain content. If a supply chain has not set an allergen baseline, a baseline for the restaurant may be set to: Allergen or Allergen unknown. Menus are analyzed to identify (by item) an allergen-level and for each menu item, a baseline is generated at an item level: Allergen, No allergen, Allergen unknown, etc. Additionally (for each social media or news source discovered) allergy blogs, tweets, online reviews, medical reports, news articles, etc. are analyzed to identify entries for a selected restaurant. The entries are parsed the content entries that are allergen related are identified. All results are combined in a weighted formula to identify a combined positive, negative, or neutral/no media weight. Additionally (as illustrated in the following logical risk table), weighted values may be used to provide an overall risk assessment for a specified restaurant in with respect to a specified allergen(s).

| Risk Table | | | |
|---|---|---|---|
| | Positive media | Negative media | No media |
| Allergen | low risk indicated | severe risk indicated | high risk indicated |
| No allergen | no risk indicated | general risk indicated | general risk indicated |
| Allergen unknown | low risk indicated | severe risk indicated | unknown |

The logical risk table is enabled to configure a memory structure (e.g., a database) to improve database access retrieval speed with respect to retrieving data from specified portions of the database.

The following implementation example (executed by system 100) describes a process for improving machine learning medical issue determination technology with respect to retrieving user information associated with user sensitivities to specified allergens including a relative risk of an allergen at a restaurant and menu item level:

A user downloads a mobile software application configured to automatically integrate user information with central database stored restaurant data to provide an individualized assessment of dining options. Additionally, the user creates one or more local profiles for dining. Creating the profile may include retrieving key allergy and sensitivity information, electronic medical data related to allergies, etc. The mobile software application is executed and a user selects a geographic location of interest to search for a restaurant. In response, the mobile software application analyzes a selected user profile with respect to listed allergens for each local restaurant and presents a ranked list based on determined allergen risk. Additionally, selecting a user profile may include executing an application for enabling a communication link (e.g., a Bluetooth connection) to automatically locate additional mobile hardware devices for selecting user profiles from the additional mobile hardware devices via the application.

Figure 2:
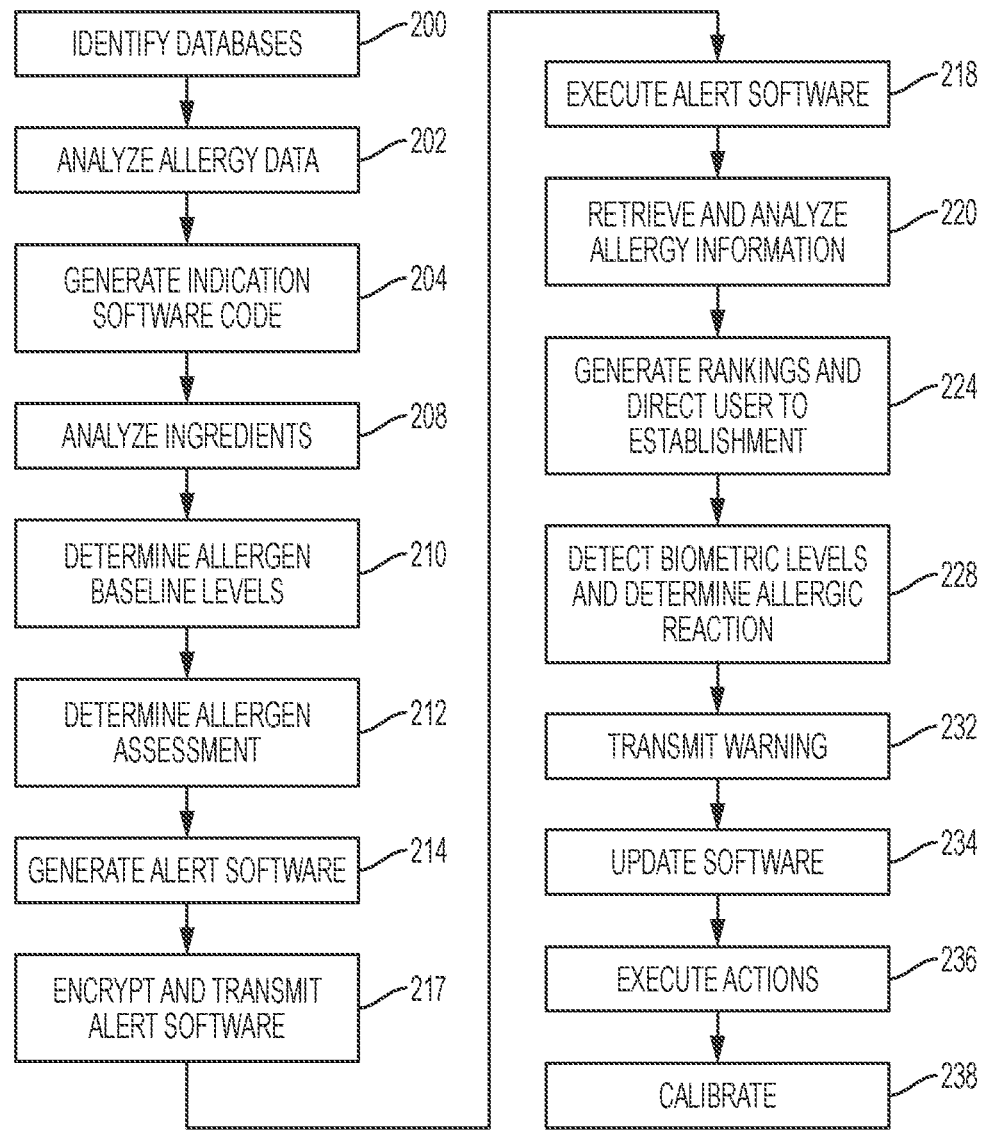
FIG. 2 illustrates an algorithm detailing a process flow enabled by the system of FIG. 1 for improving machine learning allergy risk diagnosis technology associated with enabling sensors for monitoring user conditions and executing associated actions for automatically updating software and notifying authorized personnel, in accordance with embodiments of the present invention.

FIG. 2 illustrates an algorithm detailing a process flow enabled by system 100 of FIG. 1 for improving machine learning medical issue determination technology associated with enabling sensors for monitoring user conditions and executing associated actions for automatically updating software and notifying authorized personnel, in accordance with embodiments of the present invention. Each of the steps in the algorithm of FIG. 2 may be enabled and executed in any order by a computer processor(s) executing computer code. Additionally, each of the steps in the algorithm of FIG. 2 may be enabled and executed in combination by server hardware device 104 and mobile hardware device 105. In step 200, databases are identified. The databases include data identifying menu items served by a plurality of food establishments. In step 202, allergy data is analyzed in real time via execution of natural language software code. The allergy data defines a plurality of food products associated with a plurality of potential allergens. In step 204, baseline allergen indication software code is generated based on results of the analysis of step 202. The baseline allergen indication software code is configured to define an allergen baseline indicator. In step 208, ingredients of the menu items are analyzed in real time with respect to the allergy data via execution of natural language software code and the baseline allergen indication software code. In step 210, allergen baseline levels for the ingredients are determined based on results of step 208. In step 212, an overall allergen assessment for each menu item is determined. In step 214, an allergen alert software application for alerting a user with respect to each overall allergen assessment is generated. In step 217, the allergen alert software application is optionally encrypted resulting in an encrypted allergen alert software application. Additionally, the encrypted allergen alert software application is transmitted to a plurality of mobile hardware devices. In step 218, the encrypted (or decoded) allergen alert software application is executed via a mobile hardware device. In step 220, allergy information describing allergy issues of the user is retrieved and analyzed with respect to each overall allergen assessment. In step 224, a ranked list of the plurality of food establishments is generated based on results of step 220. The ranked list is presented to the user and the user is automatically directed to a food establishment of the ranked list of food establishments. In step 228, biometric levels of the user are automatically detected via a plurality of sensor devices of the mobile hardware device. Additionally, allergy related symptoms of the user are automatically determined based on the biometric levels detected via the sensors. The allergy related symptoms indicate an initial stage of an allergic reaction with respect to a first food item being consumed by the user. Alternatively, ingredient information describing specified ingredient issues medically affecting a user may be retrieved and it may be determined that specific ingredients (served by the food establishment of the ranked list of food establishments) may be associated with the specified ingredient issues medically affecting the user. In step 232, a warning is transmitted to a hardware device of the food establishment. The warning indicates the initial stage of the allergic reaction thereby presenting feedback information for providing to an emergency services server. Alternatively, a warning indicating that the specified ingredients are associated with the specified ingredient issues. In step 234, the allergen alert software application is automatically updated based on the biometric levels of the user. In step 236, actions associated with the allergy related symptoms are executed. The action may include, inter alia:

1. Automatically signaling an emergency services server such that an ambulance is automatically dispatched to a location of the food establishment.
2. Automatically instructing the user to self-administer epinephrine to a specified body portion and automatically administering (in response to detecting that the user is placing an anti-allergen administering device of the mobile hardware device in contact with the specified body portion) the epinephrine to the specified body portion of the user.

In step 238, a calibration error of at least one sensor device is detected and automatically calibrated via a hardware calibration or a software calibration process.

Figure 3:
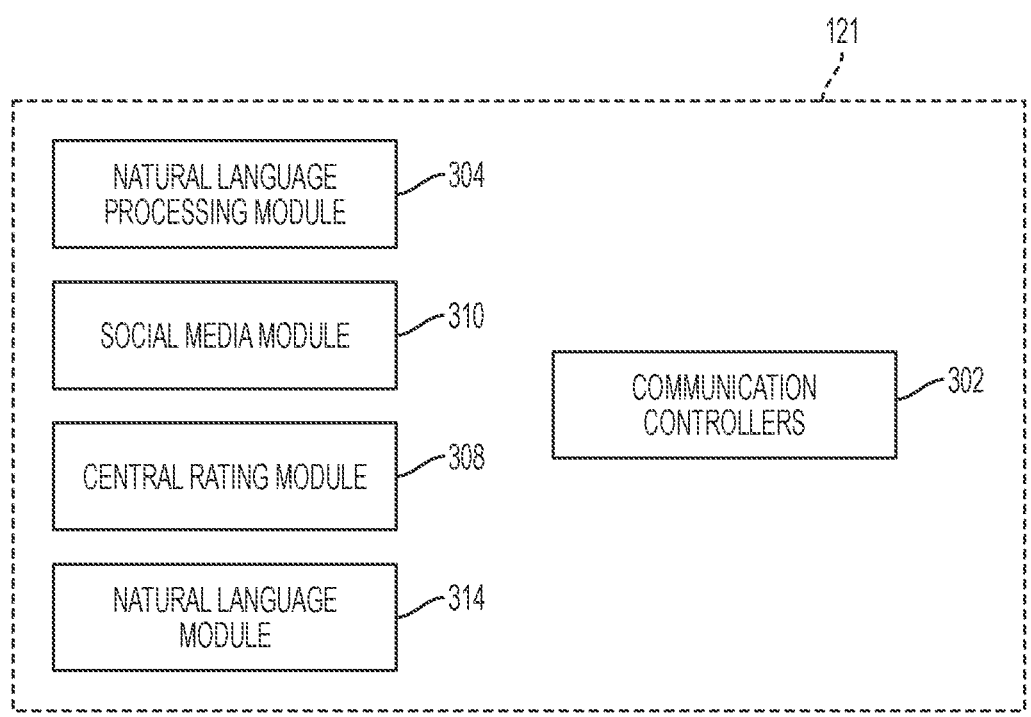
FIG. 3 illustrates an internal structural view of the software code/hardware structure of FIG. 1, in accordance with embodiments of the present invention.

FIG. 3 illustrates an internal structural view of software code/hardware structure 121 of FIG. 1, in accordance with embodiments of the present invention. Software code/hardware structure 121 includes communication controllers 302 (i.e., specialized hardware and software) communicatively linked to the following external endpoint systems: a mobile hardware device 104 (in FIG. 1), supply chain source systems, and an Internet bot for scraping social media and menu descriptions. Software code/hardware structure 121 additionally includes a natural language processing module 304, a social media module 310, a central rating module 308, and a natural language module 314. Natural language processing module 304 comprises specialized hardware and software configured to reduce supply chain information to constituent food allergy risk factors. Social media module 310 comprises specialized hardware and software configured to distill social media posts into food allergy indicators reflecting positive and negative sentiment and experience. Central rating module 308 comprises specialized hardware and software configured to combine supply chain source systems results with social media results to create overall risk ratings for each allergen. Natural language module 314 comprises specialized hardware and software configured to process menu descriptions to identify allergen indicators by identifying a description, accessing a lookup table containing recipe-based ingredients with allergen ratings by ingredient, and assessing allergen risks related to the potential supply chain paths for each ingredient. Natural language module 314 runs the following internal modules in parallel: a continuous learning module and an additional continuous learning module. The continuous learning module runs in parallel to identify supply chain sources for each ingredient and provides contamination possibilities for each ingredient based on supply chain guarantees and parallel product production/packaging. The additional continuous learning module searches for recipes by dish name to discover alternate recipes to assure that all possible risks are included on a menu item in the absence of the specific recipe used. Server hardware device 105 additionally provides access to registered users to manage individual profiles linked to mobile hardware device 104.

Figure 4:
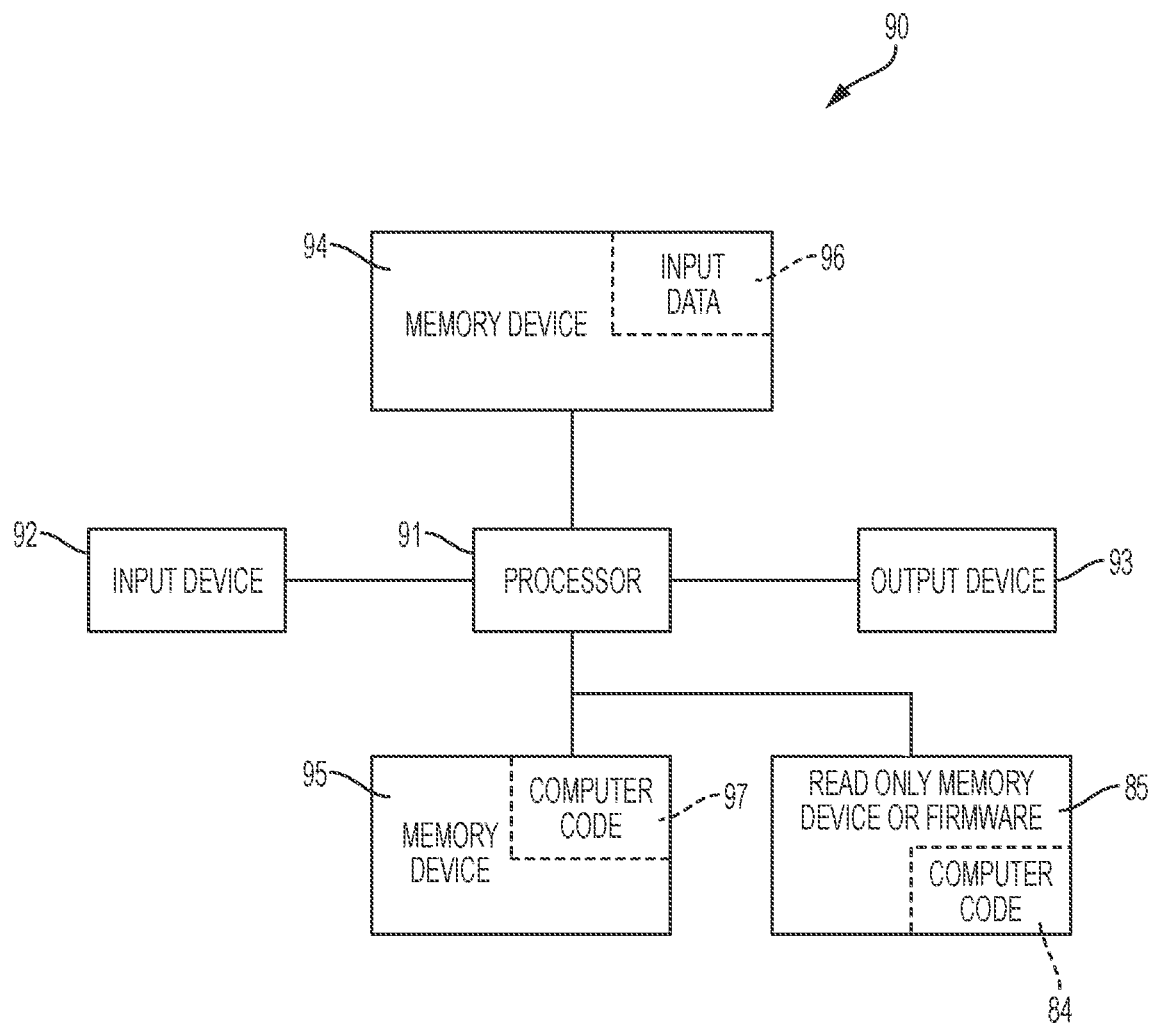
FIG. 4 illustrates a computer system used by the system of FIG. 1 for improving machine learning allergy risk diagnosis technology associated with enabling sensors for monitoring user conditions and executing associated actions for automatically updating software and notifying authorized personnel, in accordance with embodiments of the present invention.

FIG. 4 illustrates a computer system 90 (e.g., mobile hardware device 104 and/or server hardware device 105 of FIG. 1) used by or comprised by the system of FIG. 1 for improving machine learning medical issue determination technology associated with enabling sensors for monitoring user conditions and executing associated actions for automatically updating software and notifying authorized personnel, in accordance with embodiments of the present invention.

Aspects of the present invention may take the form of an entirely hardware embodiment, an entirely software embodiment (including firmware, resident software, micro-code, etc.) or an embodiment combining software and hardware aspects that may all generally be referred to herein as a "circuit," "module," or "system."

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing apparatus receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, device (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing device to produce a machine, such that the instructions, which execute via the processor of the computer or other programmable data processing device, create means for implementing the functions/acts specified in the flowchart and/or block diagram block or blocks. These computer readable program instructions may also be stored in a computer readable storage medium that can direct a computer, a programmable data processing device, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing device, or other device to cause a series of operational steps to be performed on the computer, other programmable device or other device to produce a computer implemented process, such that the instructions which execute on the computer, other programmable device, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The computer system 90 illustrated in FIG. 4 includes a processor 91, an input device 92 coupled to the processor 91, an output device 93 coupled to the processor 91, and memory devices 94 and 95 each coupled to the processor 91. The input device 92 may be, inter alia, a keyboard, a mouse, a camera, a touchscreen, etc. The output device 93 may be, inter alia, a printer, a plotter, a computer screen, a magnetic tape, a removable hard disk, a floppy disk, etc. The memory devices 94 and 95 may be, inter alia, a hard disk, a floppy disk, a magnetic tape, an optical storage such as a compact disc (CD) or a digital video disc (DVD), a dynamic random access memory (DRAM), a read-only memory (ROM), etc. The memory device 95 includes a computer code 97. The computer code 97 includes algorithms (e.g., the algorithm of FIG. 2) for improving machine learning medical issue determination technology associated with enabling sensors for monitoring user conditions and executing associated actions for automatically updating software and notifying authorized personnel. The processor 91 executes the computer code 97. The memory device 94 includes input data 96. The input data 96 includes input required by the computer code 97. The output device 93 displays output from the computer code 97. Either or both memory devices 94 and 95 (or one or more additional memory devices Such as read only memory device 96) may include algorithms (e.g., the algorithm of FIG. 2) and may be used as a computer usable medium (or a computer readable medium or a program storage device) having a computer readable program code embodied therein and/or having other data stored therein, wherein the computer readable program code includes the computer code 97. Generally, a computer program product (or, alternatively, an article of manufacture) of the computer system 90 may include the computer usable medium (or the program storage device).

In some embodiments, rather than being stored and accessed from a hard drive, optical disc or other writeable, rewriteable, or removable hardware memory device 95, stored computer program code 84 (e.g., including algorithms) may be stored on a static, nonremovable, read-only storage medium such as a Read-Only Memory (ROM) device 85, or may be accessed by processor 91 directly from such a static, nonremovable, read-only medium 85. Similarly, in some embodiments, stored computer program code 97 may be stored as computer-readable firmware 85, or may be accessed by processor 91 directly from such firmware 85, rather than from a more dynamic or removable hardware data-storage device 95, such as a hard drive or optical disc.

Still yet, any of the components of the present invention could be created, integrated, hosted, maintained, deployed, managed, serviced, etc. by a service supplier who offers to improve machine learning medical issue determination technology associated with enabling sensors for monitoring user conditions and executing associated actions for automatically updating software and notifying authorized personnel. Thus, the present invention discloses a process for deploying, creating, integrating, hosting, maintaining, and/or integrating computing infrastructure, including integrating computer-readable code into the computer system 90, wherein the code in combination with the computer system 90 is capable of performing a method for enabling a process for improving machine learning medical issue determination technology associated with enabling sensors for monitoring user conditions and executing associated actions for automatically updating software and notifying authorized personnel. In another embodiment, the invention provides a business method that performs the process steps of the invention on a subscription, advertising, and/or fee basis. That is, a service supplier, such as a Solution Integrator, could offer to enable a process for improving machine learning medical issue determination technology associated with enabling sensors for monitoring user conditions and executing associated actions for automatically updating software and notifying authorized personnel. In this case, the service supplier can create, maintain, support, etc. a computer infrastructure that performs the process steps of the invention for one or more customers. In return, the service supplier can receive payment from the customer(s) under a subscription and/or fee agreement and/or the service supplier can receive payment from the sale of advertising content to one or more third parties.

While FIG. 4 shows the computer system 90 as a particular configuration of hardware and software, any configuration of hardware and software, as would be known to a person of ordinary skill in the art, may be utilized for the purposes stated supra in conjunction with the particular computer system 90 of FIG. 4. For example, the memory devices 94 and 95 may be portions of a single memory device rather than separate memory devices.

Cloud Computing Environment

It is to be understood that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Figure 5:
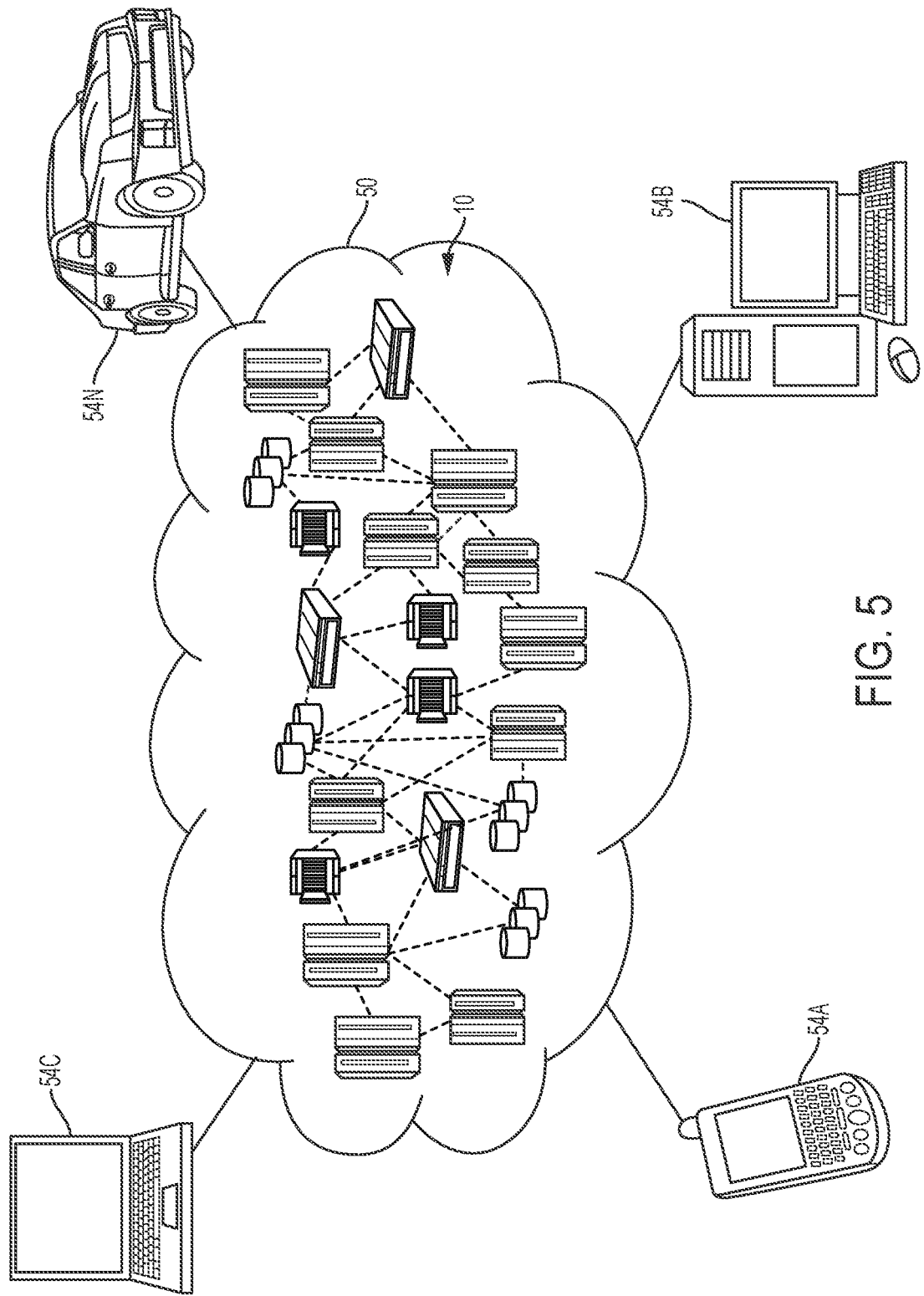
FIG. 5 illustrates a cloud computing environment, in accordance with embodiments of the present invention.

Referring now to FIG. 5, illustrative cloud computing environment 50 is depicted. As shown, cloud computing environment 50 includes one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A, 54B, 54C and 54N shown in FIG. 5 are intended to be illustrative only and that computing nodes 10 and cloud computing environment 50 can communicate with any type of computerized device over any type of network and/or network addressable connection (e.g., using a web browser).

Figure 6:
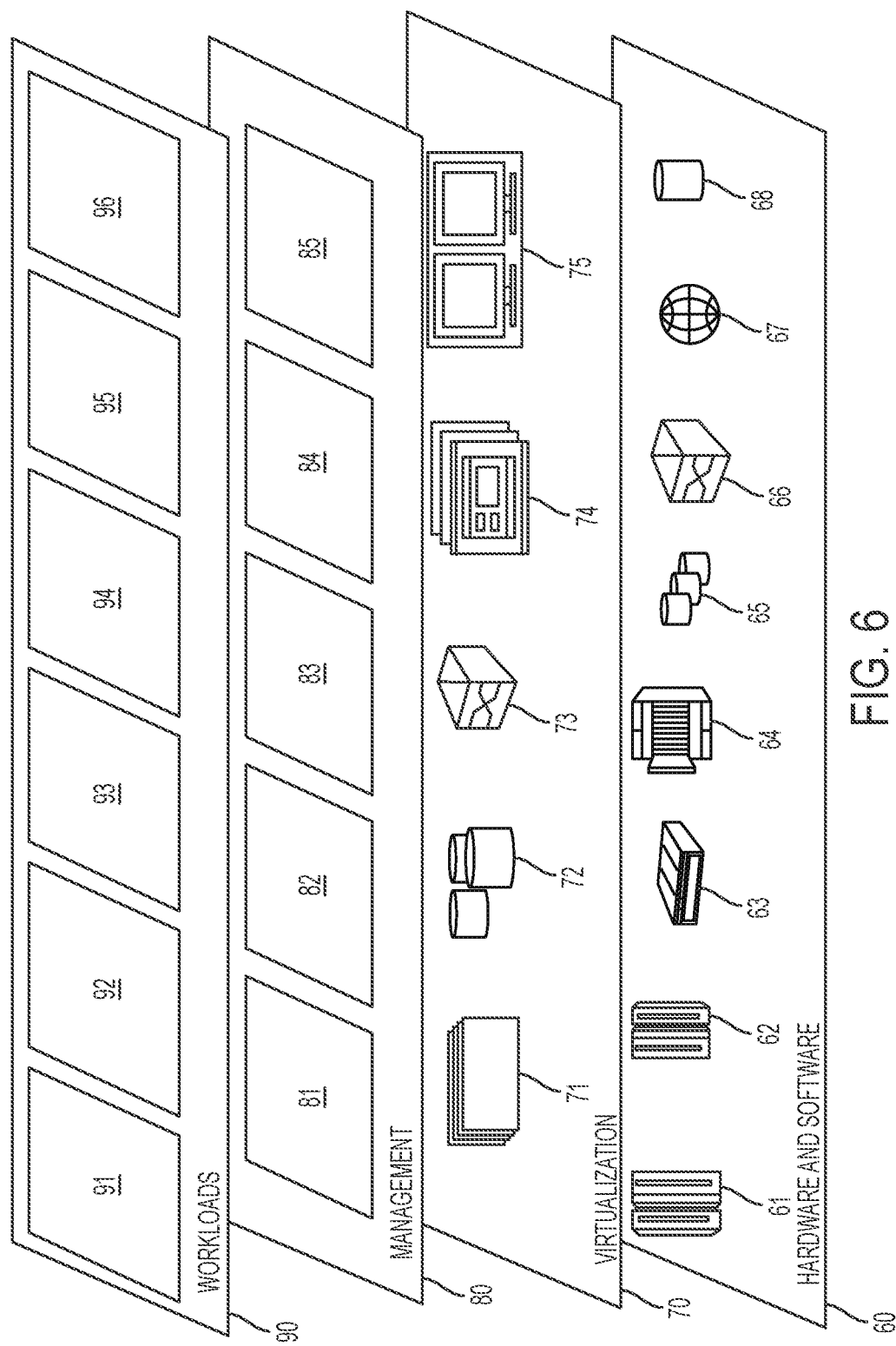
FIG. 6 illustrates a set of functional abstraction layers provided by cloud computing environment, in accordance with embodiments of the present invention.

Referring now to FIG. 6, a set of functional abstraction layers provided by cloud computing environment 50 (see FIG. 5) is shown. It should be understood in advance that the components, layers, and functions shown in FIG. 6 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 89 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and for improving machine learning medical issue determination technology associated with enabling sensors for monitoring user conditions and executing associated actions for automatically updating software and notifying authorized personnel 96.

While embodiments of the present invention have been described herein for purposes of illustration, many modifications and changes will become apparent to those skilled in the art. Accordingly, the appended claims are intended to encompass all such modifications and changes as fall within the true spirit and scope of this invention.

What is claimed is:

1. A computer program product, comprising a computer readable hardware storage device storing a computer readable program code, said computer readable program code comprising an algorithm that when executed by a processor of a server hardware device implements a machine learning allergy risk diagnosis improvement method, said method comprising:

identifying, by said processor, a plurality of databases comprising data identifying menu items served by a plurality of food establishments;

executing, by said processor, a Web scraping process associated with a simultaneous process for retrieving restaurant and menu recommendations and supplier data for suppliers of restaurants specified in said restaurant and menu recommendations;

simultaneously retrieving, by said processor in response to said executing said Web scraping process, said restaurant and menu recommendations;

simultaneously retrieving, by said processor in response to said executing said Web scraping process, social media data, allergy blog data, and medical report data associated with said restaurants;

first analyzing in real time, by said processor executing natural language software code with respect to said restaurant and menu recommendations, said social media data, said allergy blog data, and said medical report data, allergy data defining a plurality of food products associated with a plurality of potential allergens;

generating, by said processor based on results of said analyzing, baseline allergen indication software code for defining an allergen baseline indicator;

running, by said processor, restaurant recipes, of said restaurants specified in said restaurant and menu recommendations, through said natural language software code to locate items identified as allergen-containing within supply chain content of said suppliers;

second analyzing in real time, by said processor executing said natural language software code and said baseline allergen indication software code with respect to results of said running, ingredients of said menu items with respect to said allergy data;

determining, by said processor based on results of said second analyzing in real time, allergen baseline levels for said ingredients of said menu items;

determining, by said processor, an allergen baseline level for each menu item of said menu items;

generating, by said processor, an overall allergen assessment associated with each said allergen baseline level;

generating, by said processor, an allergen alert software application for alerting users with respect to each said overall allergen assessment associated with each said allergen baseline level;

generating, by said processor, a logical allergen risk table associated with a weighted risk assessment for said plurality of food establishments with respect to each said overall allergen assessment, wherein said logical allergen risk table increases an access retrieval speed of said plurality of databases with respect to retrieving said data from specified portions of the plurality of databases;

automatically directing, by said processor based on a user selection, said user to a first food establishment causing said user to proceed to said first food establishment;

enabling, by said processor, a communication link of said mobile hardware device;

locating, by said processor via said communication link, additional mobile hardware devices comprising profiles associated with said food establishment;

automatically detecting, by said processor via a plurality of sensor devices of said mobile hardware device, biometric levels of said user at said first food establishment, wherein said plurality of sensor devices comprise a video retrieval device, a blood pressure monitor, a temperature sensor, and a pulse rate monitor for said automatically detecting said biometric levels;

automatically determining, by said processor based on said biometric levels of said user, allergy related symptoms of said user indicating an initial stage of an allergic reaction with respect to a first food item being consumed by said user;

enabling, by said processor in response to said indicating said initial stage of said allergic reaction, an administrating hardware structure comprising automated medical devices and associated automated controllers to automatically activate a solenoid for initializing, enabling and causing said automated medical devices, comprising an epinephrine administering device, to automatically administer epinephrine to said user;

automatically modifying, by said processor enabling said automated medical devices and said associated automated controllers of said administrating hardware structure, biometric attributes of said user with respect to said biometric levels;

automatically detecting by said processor, a calibration error of said video retrieval device, said blood pressure monitor, said temperature sensor, and said pulse rate monitor; and automatically calibrating, by said processor, software and hardware of said video retrieval device, said blood pressure monitor, said temperature sensor, and said pulse rate monitor.

2. The computer program product of claim 1, wherein said method further comprises:
  encrypting, by said processor, said allergen alert software application resulting in an encrypted allergen alert software application; and
  transmitting, by said processor, said encrypted allergen alert software application to a plurality of mobile hardware devices.

3. The computer program product of claim 1, wherein said method further comprises:
  transmitting, by said processor, said allergen alert software application to a mobile hardware device;
  executing, by said processor via said mobile hardware device, said allergen alert software application;
  retrieving, by said processor from a user of said mobile hardware device, allergy information describing allergy issues of said user;
  third analyzing, by said processor executing said allergen alert software application, said allergy information with respect to each said overall allergen assessment;
  generating, by said processor based on results of said third analyzing, a ranked list of said plurality of food establishments;
  presenting, by said processor to said user via said mobile hardware device, said ranked list.

4. The computer program product of claim 3, wherein said method further comprises:
  transmitting, by said processor to a device of said first food establishment, a warning indicating said initial stage of said allergic reaction of said user thereby presenting feedback information for providing to an emergency services server.

5. The computer program product of claim 1, wherein said method further comprises:
  automatically updating, by said processor based on said biometric levels of said user, said allergen alert software application.

6. The computer program product of claim 1, wherein said method further comprises:
  retrieving, by said processor from a user of said mobile hardware device, ingredient information describing specified ingredient issues medically affecting said user; and
  automatically presenting by said processor to said user based on said ingredient information, a warning indicating specified ingredients of said ingredients of said menu items associated with said specified ingredient issues.

7. The computer program product of claim 1, wherein said method further comprises:
  automatically signaling, by said processor based on said allergy related symptoms of said user, an emergency services server such that an ambulance is automatically dispatched to a location of said first food establishment.

8. A server hardware device comprising a processor coupled to a computer-readable memory unit, said memory unit comprising instructions that when executed by the computer processor implements a machine learning allergy risk diagnosis improvement method comprising:
  identifying, by said processor, a plurality of databases comprising data identifying menu items served by a plurality of food establishments;
  executing, by said processor, a Web scraping process associated with a simultaneous process for retrieving restaurant and menu recommendations and supplier data for suppliers of restaurants specified in said restaurant and menu recommendations;
  simultaneously retrieving, by said processor in response to said executing said Web scraping process, said restaurant and menu recommendations;
  simultaneously retrieving, by said processor in response to said executing said Web scraping process, social media data, allergy blog data, and medical report data associated with said restaurants;
  first analyzing in real time, by said processor executing natural language software code with respect to said restaurant and menu recommendations, said social media data, said allergy blog data, and said medical report data, allergy data defining a plurality of food products associated with a plurality of potential allergens;
  generating, by said processor based on results of said analyzing, baseline allergen indication software code for defining an allergen baseline indicator;
  running, by said processor, restaurant recipes, of said restaurants specified in said restaurant and menu recommendations, through said natural language software code to locate items identified as allergen-containing within supply chain content of said suppliers;
  second analyzing in real time, by said processor executing said natural language software code and said baseline allergen indication software code with respect to results of said running, ingredients of said menu items with respect to said allergy data;
  determining, by said processor based on results of said second analyzing in real time, allergen baseline levels for said ingredients of said menu items;
  determining, by said processor, an allergen baseline level for each menu item of said menu items;
  generating, by said processor, an overall allergen assessment associated with each said allergen baseline level;
  generating, by said processor, an allergen alert software application for alerting users with respect to each said overall allergen assessment associated with each said allergen baseline level;
  generating, by said processor, a logical allergen risk table associated with a weighted risk assessment for said plurality of food establishments with respect to each said overall allergen assessment, wherein said logical allergen risk table increases an access retrieval speed of said
  plurality of databases with respect to retrieving said data from specified portions of the plurality of databases;
  automatically directing, by said processor based on a user selection, said user to a first food establishment causing said user to proceed to said first food establishment;
  enabling, by said processor, a communication link of said mobile hardware device;
  locating, by said processor via said communication link, additional mobile hardware devices comprising profiles associated with said food establishment;
  automatically detecting, by said processor via a plurality of sensor devices of said mobile hardware device, biometric levels of said user at said first food establishment, wherein said plurality of sensor devices comprise a video retrieval device, a blood pressure monitor, a temperature sensor, and a pulse rate monitor for said automatically detecting said biometric levels;
  automatically determining, by said processor based on said biometric levels of said user, allergy related symptoms of said user indicating an initial stage of an allergic reaction with respect to a first food item being consumed by said user;

enabling, by said processor in response to said indicating said initial stage of said allergic reaction, an administrating hardware structure comprising automated medical devices and associated automated controllers a controller to automatically activate a solenoid for initializing, enabling and causing said automated medical devices, comprising an epinephrine administering device, to automatically administer epinephrine to said user;

automatically modifying, by said processor enabling said automated medical devices and said associated automated controllers of said administrating hardware structure, biometric attributes of said user with respect to said biometric levels;

automatically detecting by said processor, a calibration error of said video retrieval device, said blood pressure monitor, said temperature sensor, and said pulse rate monitor; and automatically calibrating, by said processor, software and hardware of said video retrieval device, said blood pressure monitor, said temperature sensor, and said pulse rate monitor.

\* \* \* \* \*